US011241362B2

(12) United States Patent
Van Den Berg et al.

(10) Patent No.: US 11,241,362 B2
(45) Date of Patent: Feb. 8, 2022

(54) TRANSFERRING DEVICE FOR TRANSFERRING A TOXIC SUBSTANCE

(71) Applicant: SIRTEX MEDICAL LIMITED, North Sydney (AU)

(72) Inventors: Brendon Van Den Berg, North Sydney (AU); Gilman Wong, North Sydney (AU)

(73) Assignee: SIRTEX MEDICAL LIMITED, North Sydney (AU)

( * ) Notice: Subject to any disclaimer, the term of this patent is extended or adjusted under 35 U.S.C. 154(b) by 554 days.

(21) Appl. No.: 15/515,754

(22) PCT Filed: Sep. 30, 2015

(86) PCT No.: PCT/AU2015/000597
§ 371 (c)(1),
(2) Date: Mar. 30, 2017

(87) PCT Pub. No.: WO2016/049686
PCT Pub. Date: Apr. 7, 2016

(65) Prior Publication Data
US 2017/0304151 A1 Oct. 26, 2017

(30) Foreign Application Priority Data

Sep. 30, 2014 (AU) ................................. 2014903894

(51) Int. Cl.
*A61J 1/20* (2006.01)
*G21F 5/12* (2006.01)
(Continued)

(52) U.S. Cl.
CPC ............ *A61J 1/2013* (2015.05); *A61J 1/2065* (2015.05); *A61J 1/2089* (2013.01); *A61J 1/2096* (2013.01);
(Continued)

(58) Field of Classification Search
CPC ...... A61J 1/2013; A61J 1/2065; A61J 1/2089; A61J 1/2096; A61J 1/1425; A61J 1/1481;
(Continued)

(56) References Cited

U.S. PATENT DOCUMENTS 5,647,845 A * 7/1997 Haber ...................... A61J 1/10
604/32
7,862,539 B2 1/2011 Knight
(Continued)

OTHER PUBLICATIONS

International Search Report and Written Opinion of the ISA for PCT/AU2015/000597, ISA/AU, Woden Act, dated Oct. 27, 2015.

*Primary Examiner* — Philip R Wiest
(74) *Attorney, Agent, or Firm* — Harness, Dickey & Pierce, P.L.C.

(57) ABSTRACT

A device for transferring a toxic substance from a dispensing vessel to at least one receiving vessel comprising: (i) a receiving portion arranged to receive a dispensing vessel containing a toxic substance; and (ii) a transfer apparatus having a first infusion line adapted for fluid communication with the dispensing vessel to transfer a carrier fluid into said vessel and a second infusion line having one end adapted for fluid communication to withdraw and transfer the carrier fluid and the toxic substance from the dispensing vessel and the other end of the second infusion line arranged to connect with the at least one receiving vessel.

9 Claims, 4 Drawing Sheets

(51) Int. Cl.
  *G21F 5/14* (2006.01)
  *G21F 5/015* (2006.01)
  *G01F 13/00* (2006.01)
  *A61M 5/32* (2006.01)
  *A61J 1/14* (2006.01)

(52) U.S. Cl.
  CPC .............. *A61M 5/32* (2013.01); *G01F 13/00* (2013.01); *G21F 5/015* (2013.01); *G21F 5/12* (2013.01); *G21F 5/14* (2013.01); *A61J 1/1425* (2015.05); *A61J 1/1481* (2015.05)

(58) Field of Classification Search
  CPC .. A61J 5/32; G01F 13/00; G01F 5/015; G01F 5/12; G01F 5/14
  See application file for complete search history.

(56) References Cited

U.S. PATENT DOCUMENTS

| | | |
|---|---|---|
| 2007/0102044 A1 | 5/2007 | Patzek |
| 2011/0175347 A1* | 7/2011 | Okiyama ............. A61J 1/2089 285/132.1 |
| 2013/0006214 A1 | 1/2013 | Garfield et al. |

\* cited by examiner

TRANSFERRING DEVICE FOR TRANSFERRING A TOXIC SUBSTANCE

CROSS-REFERENCE TO RELATED APPLICATIONS

This application is a 371 U.S. National Stage of International Application No. PCT/AU2015/000597, filed Sep. 30, 2015, which claims the benefit of and priority to Australian Patent Application No. 2014903894, filed Sep. 30, 2014. The disclosures of the above applications are incorporated herein by reference.

TECHNICAL FIELD

The invention relates generally to the field of devices for transferring toxic substances from one vessel to another.

A specific embodiment of the invention finds particular, but not exclusive, use in the transfer of a radioactive substance from a storage vial to an administration vessel.

BACKGROUND ART

Toxic substances are, by definition, toxic to humans, animals and the environment. Even in trace amounts, toxins can have very harmful effects on humans, domesticated animals, and fish and wildlife. If not properly stored, toxins can leak into the environment contaminating the air, soil, water, or foods and foodstuffs and can produce acute or chronic adverse effects in humans or animals exposed to or ingesting these materials. Toxins can also cause mutagenic, teratogenic or carcinogenic effects.

The identification of hazardous substances and the recognition by scientific and governmental authorities and the public at large of the risks associated with toxics substances has led to the development of devices and protective measures for handling such materials. In this regard, the hazards associated with the use of toxic substances and the like has led to the development of devices for the appropriate and safe transfer of toxic substances from one container to another in order to ensure that such substances are not inadvertently exposed to the environment or to those persons handling the substances.

In some settings, patients require treatment with radioactive substances. The doses of the radioactive substance are often delivered to the treating physician in an ampule encased within a protective lead pot. However, in order to administer the radioactive substance to the patient, physicians or other personnel may be required to transfer the substance from the ampule to an administration device, such as a syringe. In order to load the syringe, the person handling the radioactive substance may be required to open not only the protective lead pot encapsulating the ampule, but the ampule itself, in order to transfer the substance manually from the ampule to the syringe. This potentially exposes the person handling the radioactive substance to radiation. Repeated exposure over numerous transfers can be very harmful to the person handling the radioactive substance; leading to radiation poisoning, cancer and in some instances can cause fatalities.

In some instances, the person handling the radioactive substance may utilise a protective shield, such as Perspex, to limit their exposure to radiation. However, in many instances, the person handling the radioactive substance may still expose their hands and arms to radiation. Therefore, eliminating, or substantially reducing, the level of exposure of a physician to radiation is desirable.

The preceding discussion of the background art is intended to facilitate an understanding of the present invention only. The discussion is not an acknowledgement or admission that any of the material referred to is or was part of the common general knowledge as at the priority date of the application.

SUMMARY OF INVENTION

It is an object of this invention to provide a transferring device for transferring toxic substances which ameliorates, mitigates or overcomes, at least one disadvantage of the prior art, or which will at least provide the public with a practical choice.

In one aspect of the invention, provided herein is a transferring device for transferring a toxic substance from a dispensing vessel to at least one receiving vessel, the transferring device comprising:
  (i) a receiving portion arranged to receive the dispensing vessel containing the toxic substance; and
  (ii) a transfer apparatus having a first infusion line adapted for communication with the dispensing vessel to transfer a carrier fluid into the vessel and a second infusion line having one end adapted for fluid communication to withdraw and transfer the carrier fluid and the toxic substance from the dispensing vessel, and the other end arranged to communicate with the at least one receiving vessel.

Infusion lines can communicate with the dispensing vessel in a variety of ways. For example the lines may either attach to a piercing portion that is adapted for penetrating the dispensing vessel. To the extent that the piercing portion is in communication with the second infusion line it must also be in communication with the contents of the dispensing vessel. It will be appreciated that in such circumstances the piercing portion that is associated with the first infusion line need not necessarily be in fluid communication with the contents of the dispensing vessel. In an alternate form the dispensing vessel may have attached thereto a sealing means such as a cap, which is adapted to receive the transfer apparatus to bring said transfer apparatus into fluid communication with the contents of the dispensing vessel. This may be achieved by the cap having located on a distal face of the cap one or more means for communicating with the contents of the dispersing vessel. Preferably the means that communicates with the second infusion line is in fluid communication with the contents of the dispensing vessel when loaded with carrier fluid. In such a form a proximal face of the cap will also include at least a means for receiving and establishing fluid communication between each of the infusion lines and the contents of the dispensing vessel. In yet another form of the invention the transfer apparatus includes at least one piercing portion in the form of a shaft through which there may exist one or more conduits that bring the transfer apparatus in fluid communication with the contents of the dispensing vessel.

In one embodiment of the invention, an outlet of the transfer apparatus is movable from a location within a body of the device to a location that allows for the outlet of the transfer apparatus to enter the dispensing vessel.

In one embodiment, the receiving portion is arranged to be removably engagable from a shielding portion configured to shield the outlet of the transfer apparatus. Preferably the receiving portion is arranged to be removably locked relative to the shielding portion.

In one embodiment, the shielding portion is prevented from disengaging from the device unless the outlet of the transfer apparatus is located in the body of the device.

In one embodiment, the receiving portion is prevented from engaging with the dispensing vessel unless the outlet of the transfer apparatus is located in the body of the device.

In one embodiment, the outlet of the transfer apparatus is prevented from extending from the body of the device unless the receiving portion has engaged the dispensing vessel.

In one embodiment, the transfer apparatus includes at least one needle.

In one embodiment, at least one of the infusion lines of the transfer apparatus includes at least one needle. The at least one needle may be hollow to provide the outlet.

In one embodiment, the toxic substance is a radioactive substance. Such a substance may be a plurality of radioactive microparticles. In an alternate form the toxic substance is a pathogen, such as a substance that is a harmful substance. For example the toxic substance may be a poison.

In one embodiment, the receiving vessel is a syringe.

In a second aspect of the invention, provided herein is a device for transferring a substance from a dispensing vessel to at least one receiving vessel comprising:
(i) a receiving portion arranged to receive a dispensing vessel containing a substance; and
(ii) a transfer apparatus having a first infusion line adapted for fluid communication with the dispensing vessel to transfer a carrier fluid into said vessel and a second infusion line having one end adapted for fluid communication to withdraw and transfer the carrier fluid and the substance from the dispensing vessel and the other end arranged to connect with the at least one receiving vessel.

In an embodiment of the second aspect of the invention, the substance is at least one of: a gas, a liquid, a fluid, an aqueous liquid, an organic liquid, a solvent, a diluent, saline, a buffer, an isotonic solution, a pharmaceutical substance, a drug, fluid for intravenous injection, culture media, an acid, an alkaline or a liquid concentrate.

In another aspect of the invention, provided herein is a transferring device for transferring a toxic substance from a dispensing vessel to at least one receiving vessel comprising:
(i) a receiving portion arranged to receive the dispensing vessel containing the toxic substance; and
(ii) a transfer apparatus having:
a first infusion line adapted to be in fluid communication with the dispensing vessel, when received upon the receiving portion, to transfer a carrier fluid into the vessel and
a second infusion line having a first end adapted to be in fluid communication with the dispensing vessel to withdraw and transfer the carrier fluid and the toxic substance therefrom, and a second end adapted to be in fluid communication with the at least one receiving vessel;
wherein the transfer apparatus is movable between an extended configuration wherein the dispensing vessel can be received thereon, and an engaged configuration wherein the dispensing vessel is locked relative to the receiving portion, allowing the transfer of the toxic substance from the dispensing vessel to a receiving vessel.

In another aspect of the invention, provided herein is a transferring device for transferring a substance from a dispensing vessel to at least one receiving vessel comprising:
(i) a receiving portion arranged to releasably receive the dispensing vessel containing the substance; and
(ii) a transfer apparatus movable between an first configuration, wherein the dispensing vessel may be received on or removed from the receiving portion, and a second configuration wherein the dispensing vessel is locked relative to the transferring device;
whereby in the second configuration the substance may be transferred from the dispensing vessel to a receiving vessel through at least one infusion line.

When in the first configuration the transfer apparatus may be in an extended configuration. When in the second configuration the transfer apparatus may be in an engaged configuration.

The dispending vessel may incorporate a shield portion, wherein the shield portion is adapted to be releasbly secured to the receiving portion. In other embodiments the shield portion may be secured to the dispensing vessel.

The at least one infusion line may have a first end which provides an outlet, wherein the outlet is caused to enter the substance in the dispensing vessel when the transfer apparatus is in the engaged configuration.

The outlet may be located within the transfer apparatus when the transfer apparatus is in the extended configuration.

The at least one infusion line may have a second end which is adapted to be connected to a receiving vessel for receiving the toxic substance in the dispensing vessel.

The transferring device may comprise a second infusion line having an outlet which enters the dispensing vessel when the transfer apparatus is in the engaged configuration, and is located within the transfer apparatus when the transfer apparatus is in the extended configuration. The second infusion line may deliver a carrier fluid through its outlet to the substance.

The present invention allows for the transfer of toxic substances between vessels while eliminating, or at least greatly reducing the likelihood of direct exposure of the operators to the toxic substance.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 1A are various views of a body of the transfer device and a shielding portion. The body of the device contains a receiving portion, a hollow shaft for receiving the transfer apparatus, a locking mechanism including a key, keyhole and channel, a gripping portion and a protective cover;

FIG. 1B depicts a dual needle transfer apparatus including first and second piercing portions and first and second infusion lines;

FIG. 1C depicts the transfer device engaging a shielding portion when in an engaged configuration;

FIG. 1D depicts the transfer device engaging a shielding portion in an extended (safety) configuration;

FIG. 1E depicts the transfer device engaging a dispensing vessel in an extended (safety) configuration;

FIG. 1F depicts the transfer device engaging both a dispensing vessel and a receiving vessel and in an engaged configuration; and FIG. 1G depicts the transfer device engaging an alternate dispensing vessel containing a substance. The body of the transfer device is in the engaged configuration and the transfer apparatus has penetrated the dispensing vessel.

DETAILED DESCRIPTION OF THE INVENTION

Those skilled in the art will appreciate that the invention described herein is susceptible to variations and modifications other than those specifically described. It is to be understood that the invention includes all such variations and modifications.

Throughout this specification, unless the context requires otherwise, the word "comprise", or variations such as "comprises" or "comprising", will be understood to imply the inclusion of a stated integer or group of integers but not the exclusion of any other integer or group of integers.

It must also be noted that, as used herein and in the appended claims, the singular forms "a," "or," and "the" include plural referents unless the context clearly dictates otherwise. Thus, for example, reference to "a infusion line" includes a plurality of such lines, and so forth.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

No 'gloss' should be taken from any term used, or defined in, the specification, to limit the scope of the embodiments or the broader inventive concept described herein. Other definitions for selected terms used herein may be found within the detailed description of the invention and apply throughout. Unless otherwise defined, all other technical terms used herein have the same meaning as commonly understood to one of ordinary skill in the art to which the invention belongs.

Features of the invention will now be discussed with reference to the following non-limiting description and examples.

An embodiment of the device of the present invention may be used to transfer a toxic substance from a dispensing vessel to at least one receiving vessel.

To simplify the description of the invention, the term "therapeutic substance in a fluid" will be used herein to include any form of substance that could reasonably be administered to a patient, such as, but not limited to, a chemical compound, a drug, a pharmaceutical substance, fluid for intravenous injection, or a radioactive substance, either dissolved in, or dispersed in, a liquid or gas.

The term "fluid" is intended to mean a substance that has no fixed shape, which yields easily to external pressure, such as a gas or (especially) a liquid.

Briefly, an embodiment of the transferring device described herein is for a transfer device for transferring a toxic substance from a dispensing vessel to at least one receiving vessel. The transferring device comprises a receiving portion arranged to receive the dispensing vessel containing the toxic substance and a transfer apparatus. The transfer apparatus includes a first infusion line arranged to transfer a carrier fluid into the dispensing vessel and a second infusion line having one end adapted for fluid communication to withdraw and transfer the carrier fluid and the substance from the dispensing vessel, and the other end arranged to connect with at least one receiving vessel. For ease of reference, the end of the second infusion line arranged to connect with the at least one receiving portion will be herein after referred to as a connecting portion.

Referring now with references to the FIGURES, FIGS. 1A to 1G show an embodiment of a transferring device (300) of the present invention, arranged to transfer a toxic substance from a dispensing vessel (328) to a receiving vessel (334), such as a syringe.

Figure 1A:
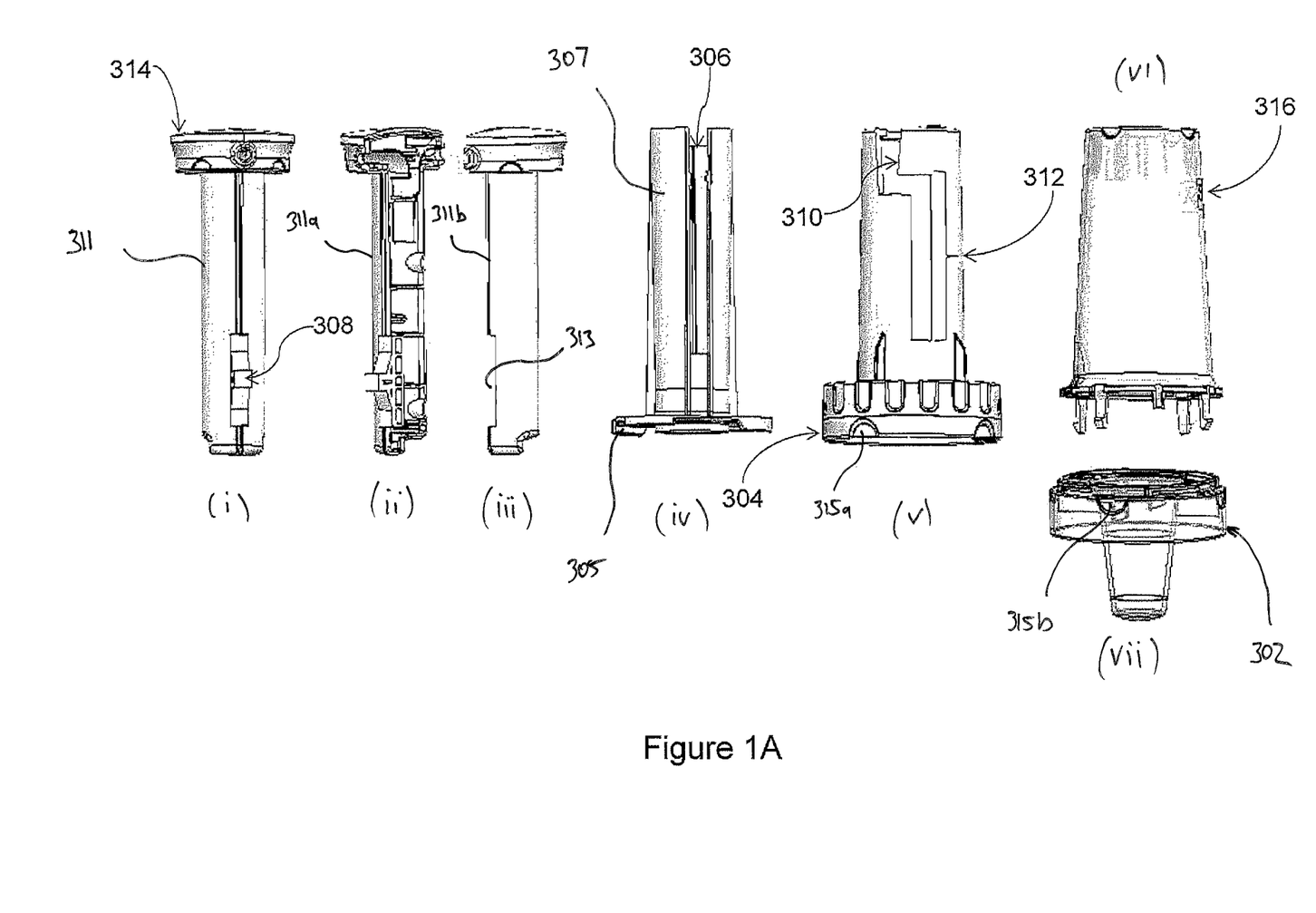
FIGS. 1A to 1G show a transfer device according to an embodiment of the present invention.

The transfer device (300) comprises a body and a shielding portion (302). The body of the device contains a receiving portion (304), a hollow shaft (306) for receiving a transfer apparatus (318), a locking mechanism comprising a key (308), keyhole (310) and a channel (312), a gripping portion (314) and a protective cover (316).

FIG. 1A(i) show a plunger (311) which provides the gripping portion (314) and key (308). An inner plunger (311a), FIG. 1A(ii), is received in an outer plunger (311b), FIG. 1A(iii), to provide the plunger (311). In so doing the key (308) provided by the inner plunger (311a) is caused to align with an aperture (313) in the outer plunger (311b), such that the key 308 protrudes therefrom.

In assembling the transfer apparatus (318) the plunger (311) is slidably received in a hollow shaft portion (307), which is shown in FIG. 1A(iv). In so doing the key (308) aligns with and is slidably received in the hollow shaft (306) of the hollow shaft portion (307).

The hollow shaft portion (307) has a flange (305) at one end. In the present embodiment the flange (305) is adapted to engage the shielding portion (302) (FIG. 1A(vii)) so that the hollow shaft portion (307) can be releasably secured to the shielding portion (302). For example, engagement of the flange (305) to the shielding portion may be a threading type engagement.

Once secured to the shielding portion (302), the hollow shaft portion (307) and the shielding portion (302) are received in the receiving portion (304) (FIG. 1A(v)). By rotating the hollow shaft portion (307) and the shielding portion (302) relative to the receiving portion (304) the key (308) is caused to align with and be received in the channel (312). When the key (308) is located in the channel (312) the shielding portion (302) is locked relative to the receiving portion (304) preventing rotation therebetween.

Upon alignment of the key (308) with the channel (312), a plurality of locking tabs (315a) on the receiving portion (304) co-operate with a plurality of locking tabs (315b) on the shielding portion (302) to releasably lock the shielding portion (302) with the receiving portion (304). This also in preventing the receiving portion (304) separating from the shielding portion (302).

FIG. 1A(vi) shows the protective cover (316) which may be applied to the transferring device once assembled.

Figure 1B:
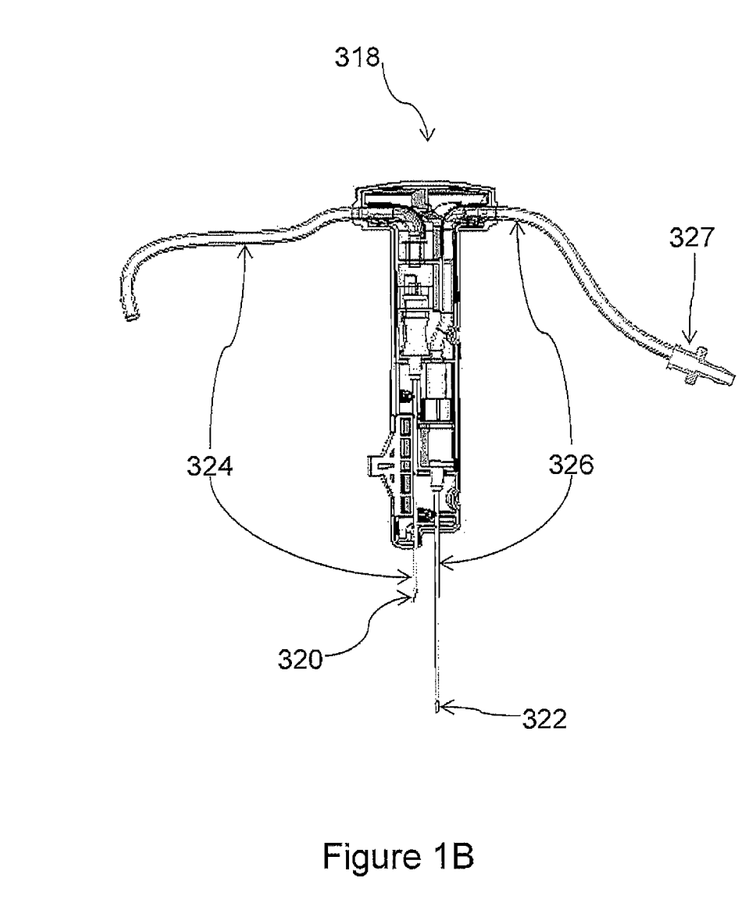
Figure 1C:
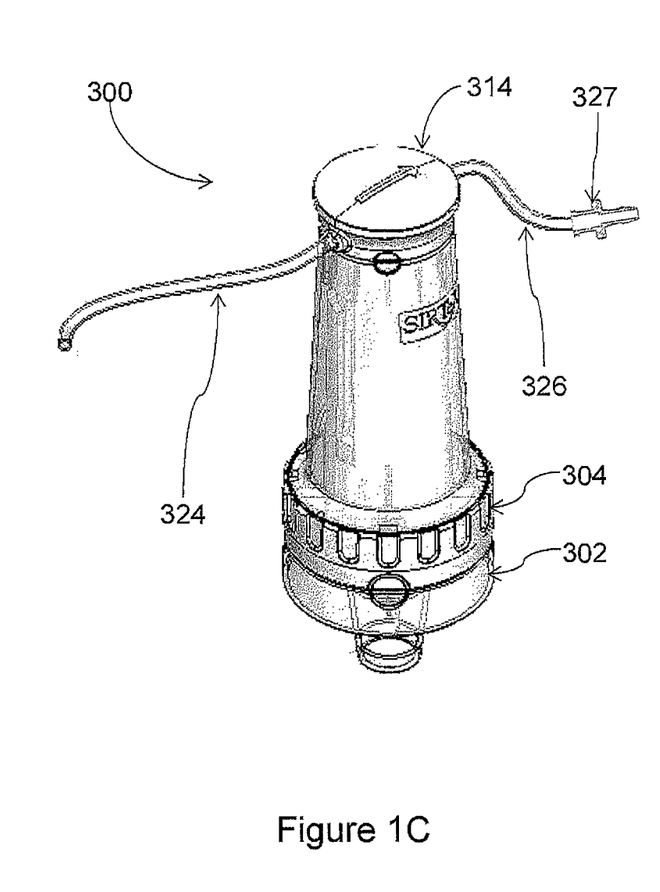
Figure 1D:
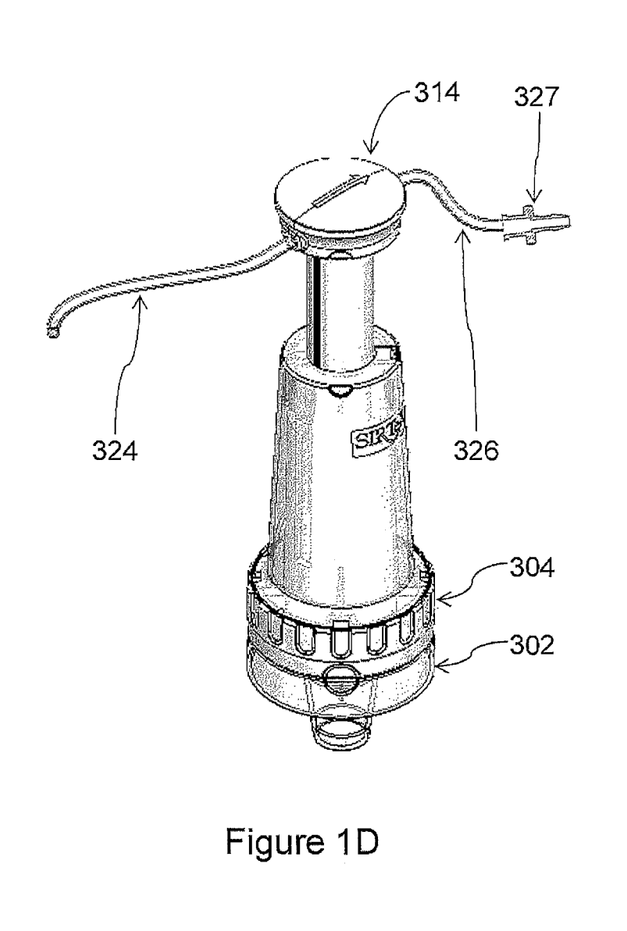
Figure 1E:
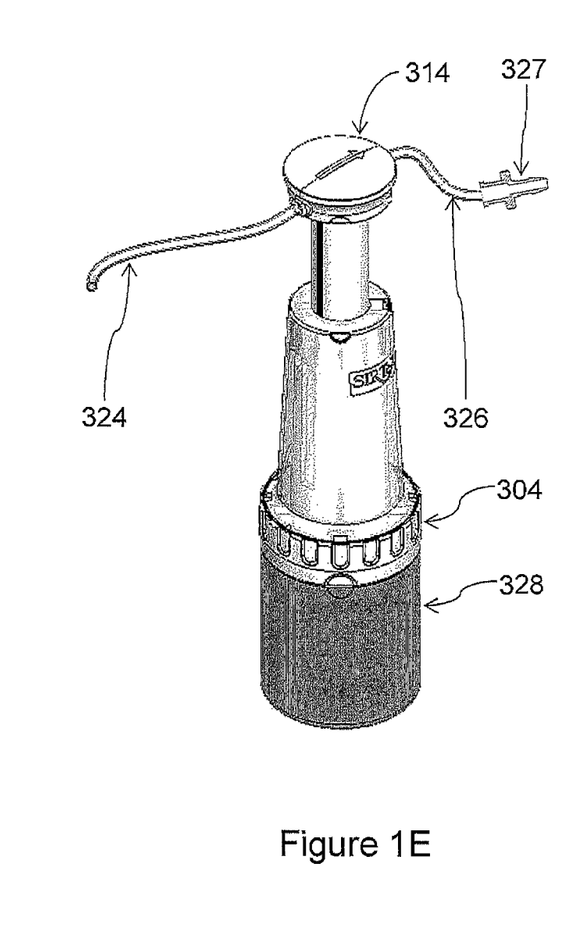

FIG. 1B depicts a dual needle transfer apparatus (318) including a first transfer apparatus outlet (320) and a second transfer apparatus outlet (322), first infusion line (324) and second infusion line (326) and a connecting portion (327). In this embodiment, the first (320) and second (322) transfer apparatus outlets provide piercing portions. Furthermore, during functioning of the transfer device one or more of the outlets (320, 322) act as an inlet.

Figures 1F, 1G:
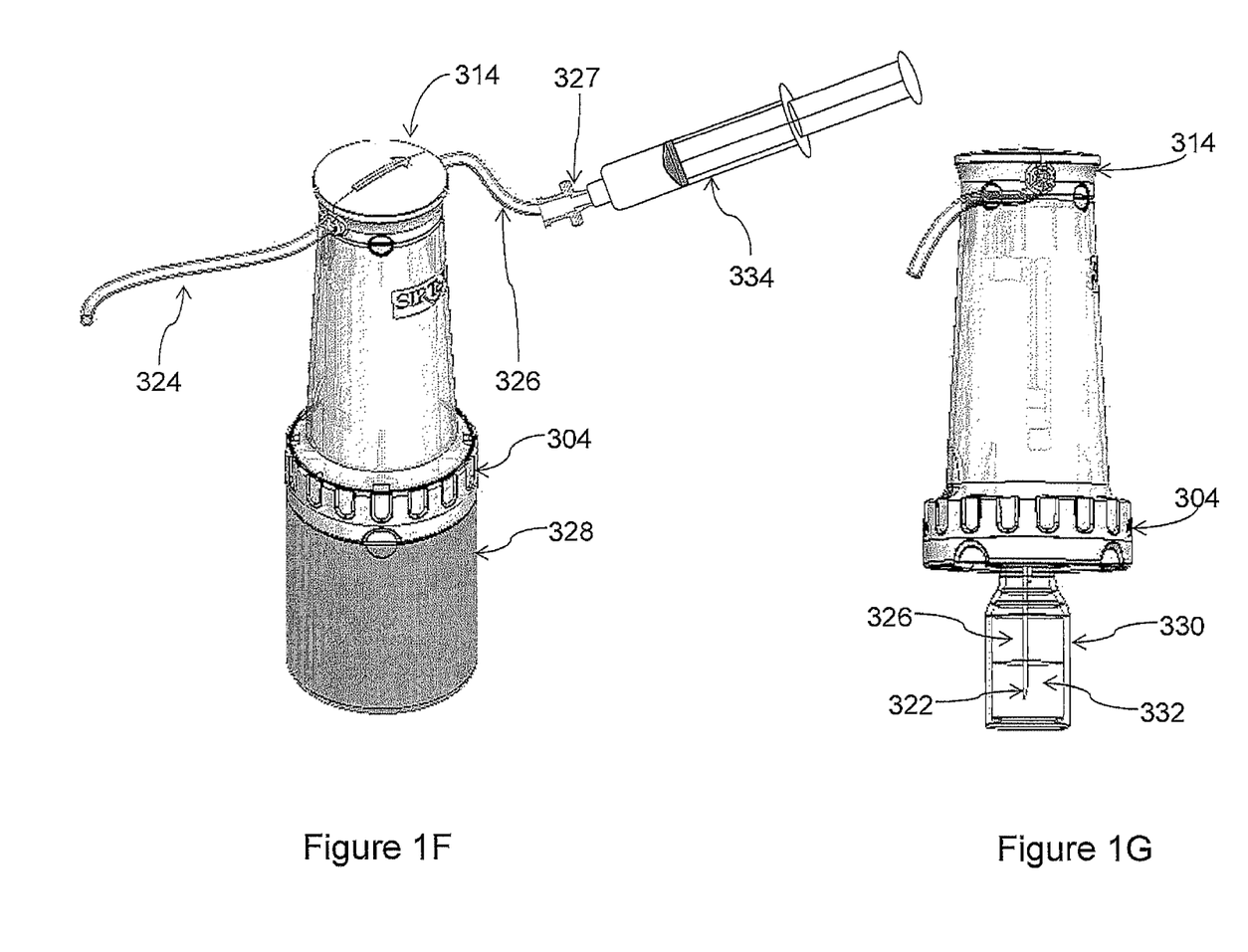

FIGS. 1C to 1F depict the transfer device (300): engaging the shielding portion (302) when in an engaged configuration (FIG. 1C); when in an extended (safety) configuration (FIG. 1D); engaging a dispensing vessel (328) when in an extended (safety) configuration (FIG. 1E); and engaging both a dispensing vessel (328) and a receiving vessel (334) when in an engaged configuration (FIG. 1F).

FIG. 1G shows the transfer device engaging an ampule (330) containing a substance (332). In use, the ampule is located inside the dispensing vessel (328) which may be in the form of a lead pot. In this figure the body of the transfer device is in the engaged configuration and the outlets (320 and 322) of the transfer apparatus (318) have penetrated the ampule (330) of the dispensing vessel (328).

In an embodiment of the invention, the outlets (320 and 322) of the transfer apparatus (318) are movable from a location within the body of the device to a location that allows for the outlets (320 and 322) of the transfer apparatus (318) to pierce the dispensing vessel (328). In this embodiment the outlets (320 and 322) provide the piercing portions.

In one embodiment, the receiving portion (304) is arranged to be removably engagable with the shielding portion (302). The shielding portion (302) is configured to shield the outlets (320 and 322) of the transfer apparatus (318). The shielding portion (302) may be prevented from disengaging from the device unless the outlets (320 and 322) of the transfer apparatus (318) are located in the body of the device, as described below.

In another embodiment, the receiving portion (304) is prevented from engaging with the dispensing vessel (328) unless the outlets of the transfer apparatus (320 and 322) are located in the body of the device. In an alternative embodiment, the outlets (320 and 322) of the transfer apparatus (318) may be prevented from extending from the body of the device unless the receiving portion (304) has engaged the dispensing vessel (328). This ensures that the dispensing vessel is not pierced until such time that the user is shielded from the contents of the dispensing vessel.

In the embodiment exemplified, a portion of the first (324) and second (326) infusion lines of the transfer apparatus are needles and the outlets of the transfer apparatus (320 and 322) are the tips of the needles (i.e. the piercing portions).

Multiple methods exist for achieving fluid communication between a device such as the transfer apparatus (318) and the dispensing vessel (328). In one form, each of the infusion lines (324 and 326) of the transfer apparatus (318) are in fluid communication with the outlets (320 and 322) which are adapted for penetrating the dispensing vessel (328). To the extent that the second outlet (322) is in communication with the second infusion line (326) it must also be in communication with the contents of the dispensing vessel (328). It will be appreciated that in such circumstances the first outlet (320) that is associated with the first infusion line (324) need not necessarily be in fluid communication with the contents of the dispensing vessel (328). In an alternate form the dispensing vessel (328) may have attached thereto a sealing means such as a cap, which is adapted to receive the transfer apparatus (318) to bring said transfer apparatus (318) into fluid communication with the contents of the dispensing vessel (328). This may be achieved by the cap having located on a distal face of the cap one or more means for communicating with the contents of the dispensing vessel (328). Preferably the means that communicates with the second infusion line (326) is in fluid communication with the contents of the dispensing vessel (328) when loaded with carrier fluid. In such a form a proximal face of the cap will also include at least a means for receiving and establishing fluid communication between each of the infusion lines (324 and 326) and the contents of the dispensing vessel (328). In yet another form of the invention the transfer apparatus (318) includes at least one piercing portion in the form of a shaft through which there may exist one or more conduits that bring the transfer apparatus (318) in fluid communication with the contents of the dispensing vessel (328).

It will be understood by the skilled addressee that the connection portion (327) which connects an end of the second infusion line with the receiving vessel (334) may be any form of suitable connecting mechanism such as, but not limited to, a luer lock, a slip luer, a luer adapter or any other suitable connecting mechanism. The connecting portion (327) connects the second infusion (326) line and the receiving vessel (334) such that they are in fluid communication.

In use, the toxic substance may be a radioactive substance such as, but not limited to, a plurality of radioactive microparticles. Other examples of toxic substances that may be used in conjunction with the device include pathogens, harmful substances or poisons.

In use, an example of a suitable receiving vessel (334) may be a syringe.

Considering the present embodiment, in use, when the receiving portion (304) has engaged the shielding portion (302), the transfer apparatus (318) is housed within the body of the device. As a safety feature, before the shielding portion (302) can disengage from the receiving portion (304), the transfer apparatus (318) must be in the extended configuration allowing the shielding portion (302) to be disengaged. This is achieved by the configuration of the locking mechanism (308, 310 and 312). The locking mechanism (308, 310 and 312) in this embodiment is of the key and keyhole type. When the body of the transfer device is in the extended position, the piercing portions (320 and 322) are housed within the body and are not exposed.

The extended configuration is achieved by manually moving the gripping portion (314) of the body away from the receiving portion (304), longitudinally along the body portion, positioning the body into the extended configuration. As this occurs the key (308) moves along the length of the channel (312). Once the body is fully extended, the key (308) is able to access the keyhole (310). Upon rotating the shield portion (302) the key (308) enters the keyhole (310). As this occurs the gripping portion can move further laterally. By depressing locking tabs (315) and rotating the shield portion (302) the shielding portion (302) can disengage and separate from the receiving portion (304).

The dispensing vessel (328) can be releasably secured to the receiving portion (302), such that the dispensing vessel (328) can be locked into place relative to the transferring device When the key (308) is in the upper part of the channel (312) the shield portion (302) and receiving portion (304) are locked relative to each other. The plunger 311 may then be returned to the engaged position by an operator manually pressing down on the gripping portion (314). As this occurs, the outlets (320 and 322) of the transfer apparatus (318), (i.e. the piercing portions), are pushed towards the dispensing vessel (328). When sufficient force has been applied, the outlets (320 and 322) pierce the lid of the ampule (330), penetrating the dispensing vessel/ampule (328/330) and inserting the outlets (320 and 322) of the transfer apparatus (318) into the dispensing vessel/ampule (328/330). The body of the device is now in the engaged configuration and is capable of transferring the substance from the dispensing vessel/ampule (328/330) into the receiving vessel (334).

It is to be understood that alternative locking mechanisms are within the scope of the present invention.

In use, the first outlet (320) is in fluid communication with the first transfer infusion line (324) which is used to inwardly transfer the carrier fluid into the dispensing vessel/ampule (328/330). The substance (332) contained within the dispensing vessel/ampule (328/330) becomes mixed/dispersed in the carrier fluid. The inward transfer of the carrier fluid into the dispensing vessel/ampule (328/330) then forces the carrier fluid and substance (332) into the second transfer infusion line (326), transferring the fluid and substance (332) to the receiving vessel (334).

The device of the present invention finds particular, but not exclusive use, in the transfer of radioactive microparticles from a storage vessel, such as the ampule (330), to the receiving vessel, such as a syringe.

Selective Internal Radiation Therapy (SIRT)

Selective internal radiation therapy (SIRT) is the intra-arterial delivery of radioactive microparticles to tumours, which has an established therapeutic role in the management of inoperable primary and metastatic liver tumours.

Microparticles

The terms "microparticle" and "microsphere" are used interchangeably and are used in this specification as an example of a particulate material, however they are not intended to limit the invention to the administration of microspheres, as the person skilled in the art will appreciate that the shape of the particulate material while preferably without sharp edges or points that could damage the patients arteries or catch in unintended locations, is not limited to spheres. Nor should the term microsphere be limited to spheres. Preferably the particulate material is substantially spherical, but need not be regular or symmetrical in shape.

The microspheres also need not be limited to any particular form or type of microparticle. Any microparticle may be administered using the device as described herein. An example of a suitable microparticle may include the type capable of receiving a radionuclide such as through impregnation, absorbing, coating or more generally bonding the particles together. An example of a suitable radionuclide includes yttrium-90 (Y-90).

The microparticles may prepared as polymeric particles, or prepared from ceramic particles or glass.

SIR-Spheres® microspheres are a trademarked product and are an example of a radioactive microparticle. They are polymeric particles usually dispersed in water for administration to the patient.

Embodiments of the device of the present invention find particular, but not exclusive use, in the transfer of radioactive microparticles, such as SIR-Spheres® microspheres from a storage ampule to an administration syringe. In this example of use, the radioactive microparticles are delivered to a physician in an ampule (330) contained within a dispensing vessel such as a protective lead pot (328). The physician then removes the lid of the lead pot to reveal the ampule (330). The physician then engages the transfer device (300) to safely transfer the radioactive substance from the ampule (330) to the syringe (334).

Although the exemplified specific use of the device described herein involves the transfer of radioactive microparticles from one vessel to another, a person skilled in the art will understand that the present invention can be used to transfer any type of toxic fluid substance such as, but not limited to a pathogen, a harmful substance or a poison. In this embodiment, exposure of the operator of the device to the toxic substance being transferred is prevented. The device also prevents the release of the toxic substance being transferred into the environment.

A person skilled in the art will appreciate that the embodiments and broader invention described herein is not only useful for the prevention of the release of a toxic substance being transferred out of the transfer system, but can also be easily and readily configured to prevent substances from getting in to the transfer system.

Therefore, in another embodiment, the device of the present invention may include a transferring device for aseptically transferring a substance from a dispensing vessel (328/330) to at least one receiving vessel (334), the transferring device comprising a receiving portion (304) arranged to receive the dispensing vessel (328) containing the substance (332), at least one outlet (320/322) arranged to pierce the dispensing vessel/ampule (328 and 330). The device also includes a connecting portion (327) arranged to receive at least one receiving vessel, and further includes a transfer apparatus (318). The transfer apparatus (318) includes a first infusion line (324) arranged to transfer a carrier fluid into the dispensing vessel (330) and a second infusion line (326) arranged to transfer the carrier fluid and the substance from the dispensing vessel (330) to the at least one receiving vessel.

In this embodiment, the transferring device may be used to transfer a substance from one vessel to another wherein the substance is at least one of a gas, a liquid, a fluid, an aqueous liquid, an organic liquid, a solvent, a diluent, saline, a buffer, an isotonic solution, a pharmaceutical substance, a drug, fluid for intravenous injection, culture media, an acid, an alkaline or a liquid concentrate.

In this embodiment, the substance contained within the dispensing vessel (328/330) need not be a toxic substance. Instead, the device can be used in a manner to prevent external substances from contaminating the substance being transferred. In this embodiment, the device (300) and receiving vessel (334) are preferably sterile such that the substance is not contaminated by contaminants within the device (300) or receiving vessel (334).

In use, this embodiment of the transferring device may find particular, but not exclusive use, in the transfer of sterile substances such as those used in laboratories and hospital settings. For example, the device (300) may find use in a laboratory wherein a laboratory technician may use the device (300) to aseptically transfer sterile tissue culture media from one vessel to another. In this example, the tissue culture media may be a concentrate and the carrier fluid used to transfer the media from the dispensing vessel/ampule (328/330) to the receiving vessel (334) may be a diluent.

Other examples may include aseptically transferring a sterile powder, such as powdered compositions of phosphate buffered saline (PBS), from a dispensing vessel (328) to a receiving vessel (334), wherein the carrier fluid is used to transfer the powdered PBS to the receiving vessel (334) is a sterile diluent.

Other examples may include aseptically transferring a sterile pharmaceutical substance, such as liquid or powdered vaccine, from a dispensing vessel (328) to a receiving vessel (334) such as a syringe, wherein the carrier fluid used to transfer the pharmaceutical substance to the syringe is a sterile diluent for injection.

A person skilled in the art will appreciate that the present invention is not limited by size and therefore variations in dimensions of the invention can be employed depending on required use of the device. The device (300) may be configured to receive any sized dispensing vessel/ampule (328/330), including but not limited, to ampules of various sizes ranging from less than 1 ml to more than 1000 ml. The device may also be configured to transfer substances to any type of suitable receiving vessel (334) such as, but not limited to, a syringe, an ampule, a Schott bottle, a falcon tube, a specimen jar or any other suitable container.

The invention claimed is:

1. A transferring device for transferring a toxic substance from a dispensing vessel to at least one receiving vessel, the transferring device comprising:
   (i) a receiving portion arranged to receive the dispensing vessel containing the toxic substance; and
   (iii) a transfer apparatus having a first infusion line adapted for fluid communication with the dispensing vessel to transfer a carrier fluid into said vessel and a second infusion line having one end adapted for fluid communication to withdraw and transfer the carrier fluid and the toxic substance from the dispensing vessel, and the other end of the second infusion line arranged to communicate with the at least one receiving vessel, an outlet of the transfer apparatus is movable from a location within a body of the device to a location that allows for the transfer apparatus to enter the dispensing vessel.

2. The device according to claim 1 wherein the receiving portion is arranged to be removably engagable from a shielding portion configured to shield the outlet of the transfer apparatus.

3. The device according to claim 2 wherein the receiving portion is arranged to be removably locked relative to the shielding portion.

4. The device according to claim 2 wherein the shielding portion is prevented from disengaging from the device unless the outlet of the transfer apparatus is located in the body of the device.

5. The device according to claim 1 wherein the receiving portion is prevented from engaging with the dispensing vessel unless the outlet of the transfer apparatus is located in the body of the device.

6. The device according to claim 1 wherein the outlet of the transfer apparatus is prevented from extending from the body of the device unless the receiving portion has engaged the dispensing vessel.

7. The device according to claim 1 wherein the transfer apparatus comprises at least one needle to provide the outlet.

8. The device according to claim 1 wherein the toxic substance is one of a radioactive substance, a radioactive substance including a plurality of radioactive microparticles, a pathogen, a harmful substance, or a poison.

9. The device according to claim 1 wherein the receiving vessel is a syringe.

* * * * *